US00PP33947P3

(12) United States Plant Patent
MacGregor et al.

(10) Patent No.: US PP33,947 P3
(45) Date of Patent: Feb. 8, 2022

(54) ***GERANIUM* PLANT NAMED 'MACGER001'**

(50) Latin Name: ***Geranium pratense* x *Geranium psilostemon***
Varietal Denomination: MACGER001

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 17/178,448

(22) Filed: Feb. 18, 2021

(65) Prior Publication Data

US 2021/0259145 P1 Aug. 19, 2021

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/42; A02H 6/42
See application file for complete search history.

(56) References Cited

PUBLICATIONS

UPOV hit on *Geranium* plant named 'MACGER001', QZ PBR 20200533, filed Feb. 18, 2020.*
Geranium 'Dark Eyes', downloaded from pressreader.com/uk/gardens-illustrated-magazine/20191210/281977494485018 on Oct. 26, 2021.*
CPVO Application Consultation, Application No. 20200533, filed Feb. 18, 2020 on a *Geranium* plant named, 'MacGer001'.*

* cited by examiner

*Primary Examiner* — Anne Marie Grunberg
(74) *Attorney, Agent, or Firm* — Samuel R. McCoy, Jr.

(57) ABSTRACT

'MACGER001' is a new and distinctive variety of *Geranium* hybrid plant which is characterized by dark greyed-green foliage that is suffused with bronze and vibrant red-purple flowers with very dark purple venation and floral eye. The new variety propagates successfully by stem cuttings and tissue culture and has shown to be uniform and stable in the resulting generations from asexual propagation.

2 Drawing Sheets

Latin name of the genus and species: The Latin name of the genus and species of the novel variety disclosed herein is *Geranium pratense* x *Geranium psilostemon.*

Variety denomination: The inventive variety of *Geranium* hybrid disclosed herein has been given the variety denomination 'MACGER001'.

CROSS REFERENCE TO RELATED APPLICATIONS

This application is related to the Community Plant Variety Rights application number 2020/0533, filed Feb. 18, 2020, which is herein incorporated by reference.

BACKGROUND OF THE INVENTION

Parentage: 'MACGER001' is the result of a controlled cross-pollination breeding program carried out by the inventors at their commercial nursery in Kirkcudbright, Scotland, in the summer of 2015. The inventors performed a controlled cross-pollination of the emasculated seed parent, an unnamed *Geranium pratense* plant (unpatented), with an unnamed *Geranium psilostemon* plant (unpatented), the pollen parent. Said pollination was performed in an insect proof environment. Seed from said cross was harvested, then germinated, and the resulting seedlings were then grown to a mature size in a protected poly tunnel greenhouse. In October of 2015, the inventors selected the new *Geranium* cultivar for its unique flower color and dark foliage. This new and distinctive cultivar was given the name 'MACGER001'.

Asexual Reproduction: Asexual reproduction of 'MACGER001' was first accomplished in October of 2015 by way of vegetative division and subsequently by way of meristematic tissue culture micro propagation at a laboratory in Rijswijk, the Netherlands. Four successive generations have shown that the unique features of the instant cultivar are stable and reproduce true to type.

SUMMARY OF THE INVENTION

The cultivar 'MACGER001' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geranium* cultivar, 'MACGER001'.

1. *Geranium* 'MACGER001' exhibits dark greyed-green foliage that is suffused with a dark bronze coloration; and
2. *Geranium* 'MACGER001' exhibits foliage that is margined greyed-purple; and
3. *Geranium* 'MACGER001' exhibits vibrant red-purple flowers with very dark purple veins radiating outward from a very dark purple floral eye.

BOTANICAL DESCRIPTION OF THE PLANT

Figure 1:
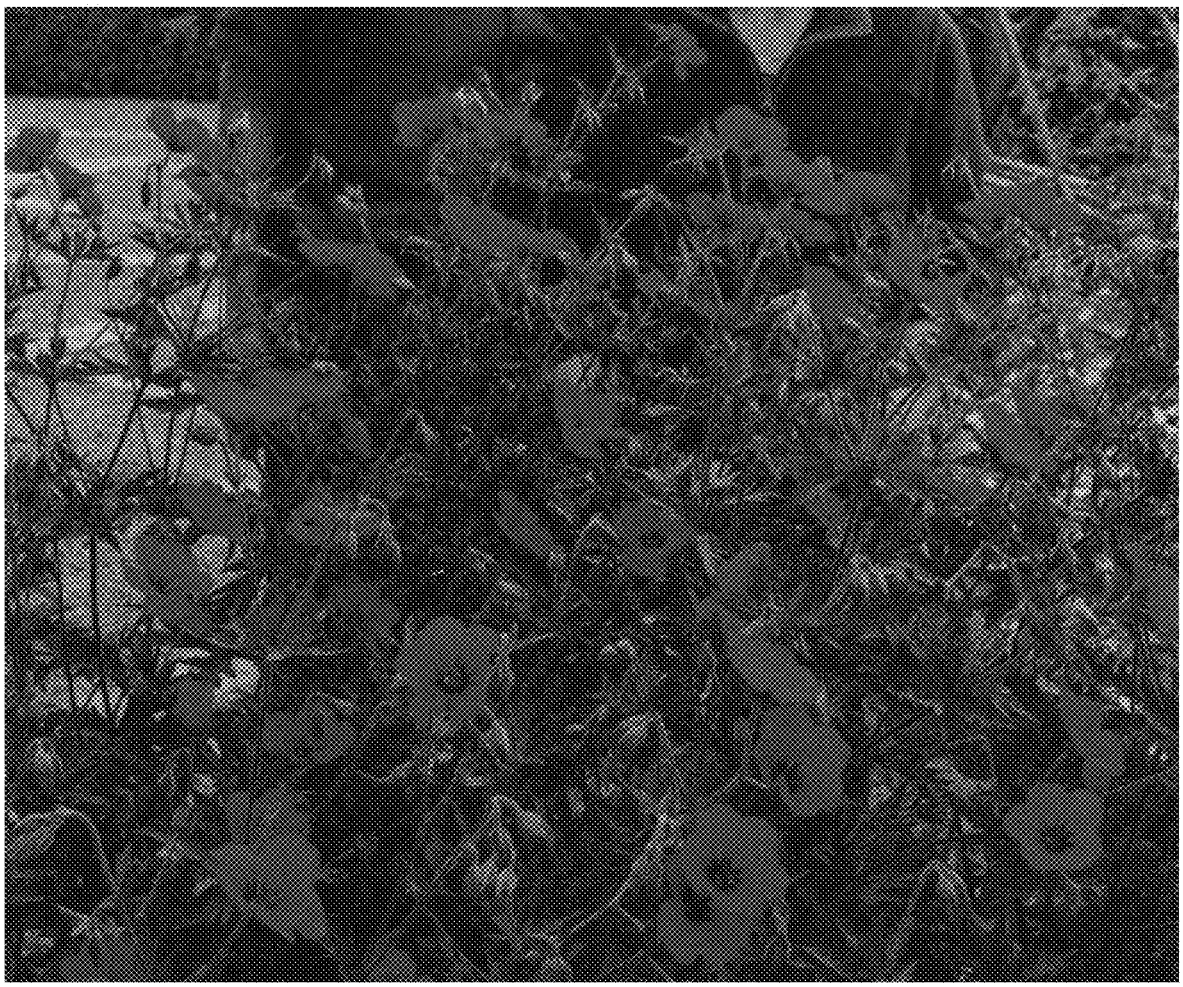
FIG. 1 shows, as nearly true as it is reasonably possible to make the same in color illustrations of this type, the typical foliage and growth characteristics of the new cultivar, 'MACGER001'.
Figure 2:
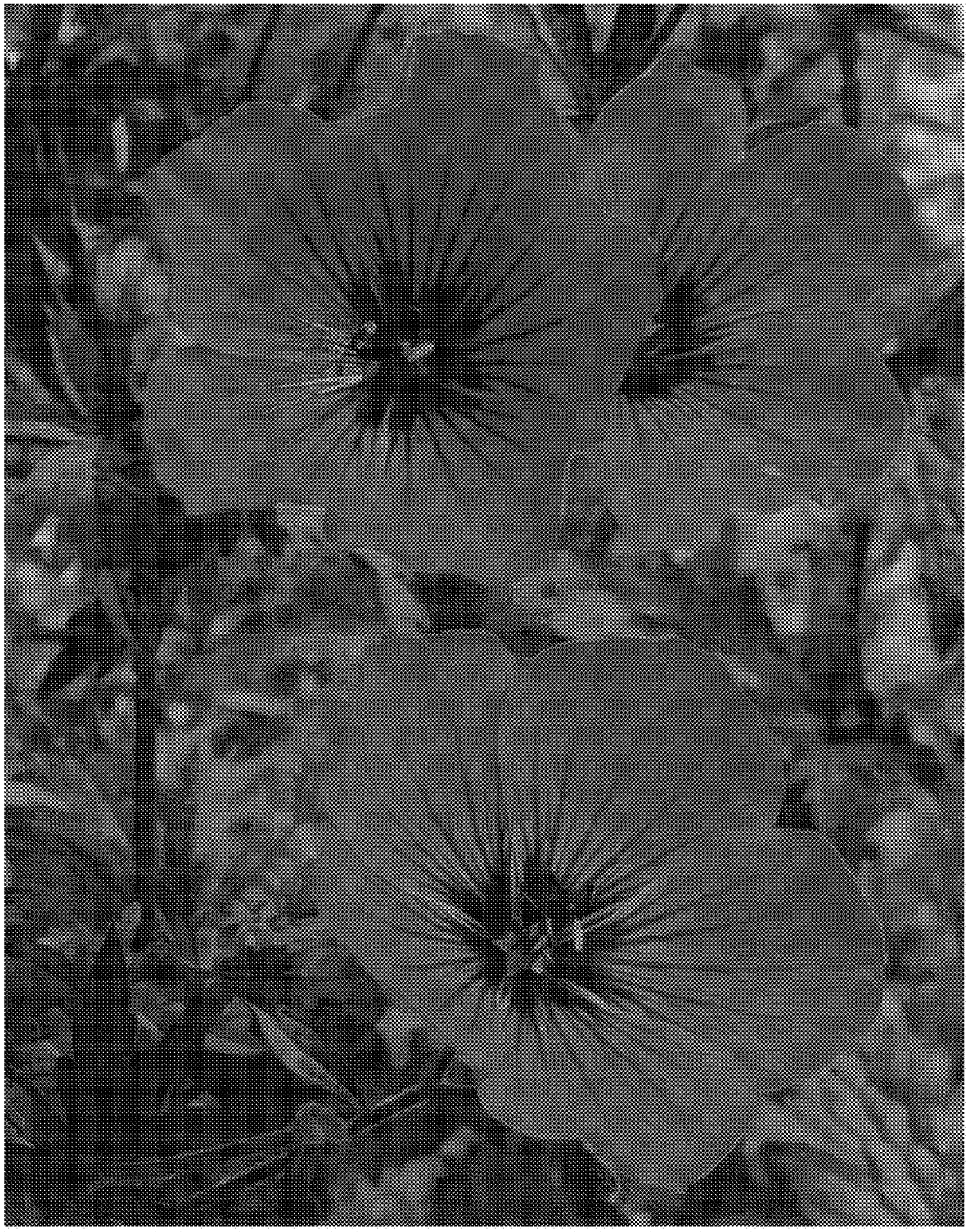
FIG. 2 shows, as nearly true as it is reasonably possible to make the same in color illustrations of this type, the typical flower of the plant in FIG. 1.

The following is a detailed botanical description of a new and distinct variety of *Geranium* plant known as 'MACGER001', based upon observations of 12-month-old plants grown outdoors in Kirkcudbright, Scotland. Plants were grown with full sun to partial shade exposure and subsisted on natural rainfall with supplemental irrigation provided during periods of dry weather. Plants were grown in a nutrient-rich compost but were otherwise not given any supplemental fertilizer. No chemical pest treatments were given to the plants. Observation data was recorded in May of 2021.

A botanical description of 'MACGER001' and comparisons with the parents and most similar variety of common knowledge are provided below.

General plant description:

*Growth habit*.—Broad-spreading herbaceous perennial with flowering stems arising from the base, and inflorescence held within and at the foliar plane.

*Plant profile*.—Globular.

*Height*.—31.8 cm to the top of the foliar plane; 32.0 cm to the top of the floral plane.

*Spread*.—61.7 cm.

*Plant vigor*.—Very vigorous.

*Growth rate*.—Fast growing.

*Propagation*.—Method — Meristematic tissue culture. Time to initiate rooting — Approximately 10 to 14 days at an average ambient temperature of 22 degrees Celsius. Time to produce flowering plant from rooted cutting — Approximately 4 months in a 15 cm container.

*Pest resistance and susceptibility*.—Plants have not been observed to be any more or less susceptible or resistant to pathogens and pests known to effect *Geranium* sp.

*Environmental tolerances*.—Adapt to, at least, USDA Zones 5 to 9 and temperatures ranging from minus 23 degrees Celsius to 35 degrees Celsius; moderate tolerance to rain; moderate tolerance to wind.

Root system:

*Description*.—A moderately dense network slightly fleshy, fibrous lateral roots.

*Rooting habit*.—Moderately branched and evenly distributed throughout the soil profile.

*Root diameter*.—2.0 mm at the base, on average.

*Texture*.—Smooth; glabrous.

*Color*.—Greyed-white, nearest to RHS 156D.

Stem:

*Branching habit*.—Basally and laterally branched; moderately free branching.

*Number of primary (main) stems per plant*.—2.

*Number of secondary (lateral) branches per plant*.—1.

*Attitude*.—Upright, at an average angle of 5 degrees from vertical.

*Aspect*.—Rounded.

*Length*.—53.8 cm.

*Diameter*.—0.4 cm.

*Internode length*.—8.8 cm.

*Texture*.—Densely covered with short, glandular hairs; hairs are colored greyed-white, nearest to RHS 156D, and are 0.8 mm long, on average.

*Luster*.—Moderately glossy.

*Strength*.—Strong.

*Color, juvenile*.—Yellow-green, nearest to RHS 144D; suffused with greyed-purple, proximally, nearest to a mixture of RHS 185B an 185C.

*Color, mature*.—Greyed-purple, nearest to RHS N186C.

*Color at internodes*.—Greyed-purple, nearest to RHS 183D; suffused with yellow-green, nearest to RHS N144B.

Foliage:

*Arrangement*.—Leaves are borne both basally and on stems; basal leaf arrangement is alternate and leaves on stems are arranged alternately.

*Basal leaves*.—Attachment — Petiolate. Division — Simple. Leaf shape — Deeply palmate, with an average of seven deeply cleft lobes, and a reniform to near orbicular profile. Lobes — Depth of sinuses — Deep. Sinus orientation — Convergent. Dimensions — 18.4 cm long, excluding the petiole, and 19.6 cm wide. Leaf attitude — Upright and outward, at an average angle of 45 degrees to vertical. Leaf apex — Acute. Leaf base — Hastate with basal lobes touching. Leaf margin — Coarsely serrate. Texture, adaxial and abaxial surfaces — Slightly rugose; pubescent. Pubescence, adaxial surface — Moderately covered with short hairs with an average length of 0.2 mm; colored greyed-white, nearest to RHS 156D. Pubescence, abaxial surface — Sparsely covered with short hairs with an average length of 0.2 mm; colored greyed-white, nearest to RHS 156D. Luster, adaxial surface — Very slightly glossy. Luster, abaxial surface — Very slightly glossy. Color — Juvenile foliage color, adaxial surface — Yellow-green, nearest to a mixture of RHS 144A and 144B; narrowly margined greyed-orange, nearest to a mixture of RHS 177A and 177B. Juvenile foliage color, abaxial surface — Yellow-green, nearest to RHS 144B; narrowly margined greyed-orange, nearest to a mixture of RHS 177A and 177B. Mature leaf color, adaxial surface — Greyed-green, nearest to RHS N189A yet slightly darker; narrowly margined and tipped brown, nearest to RHS 200A. Mature leaf color, abaxial surface — Green, nearest to RHS NN1 37D; narrowly margined and tipped greyed-orange, nearest to a mixture of RHS 178A and 178B. Venation — Type — Palmate. Vein color, adaxial surface — Green, nearest to RHS NN137D. Vein color, abaxial surface — Yellow-green, nearest to RHS N148B. Petiole — Length — 21.6 cm. Diameter — 0.4 cm. Strength — Strong. Texture, adaxial and abaxial surfaces — Sparsely covered with soft hairs, becoming moderately pubescent towards the proximal end of the petiole; average length of hairs is 0.2 cm; colored greyed-white, nearest to RHS 156D. Luster, adaxial and abaxial surfaces — Glossy. Color, adaxial surface — Greyed-purple, nearest to RHS 183A; suffused with yellow-green towards the distal end of the petiole, nearest to RHS 144B. Color, abaxial surface — Greyed-purple, nearest to RHS 183B; suffused with yellow-green towards the distal end of the petiole, nearest to RHS 144B. Stipules — General — Two leafy stipules present at the base of each leaf. Shape — Ovate. Length — 0.9 cm. Diameter — 0.3 cm. Apex — Acuminate. Base — Broad cuneate. Margins — Serrate. Texture, adaxial and abaxial surfaces — Densely covered with soft hairs; average length of hairs is 0.1 cm; colored white, RHS N155A. Luster, adaxial and abaxial surfaces — Moderately glossy. Color, adaxial surface — Greyed-red, nearest to RHS 183A; main vein is brown, nearest to RHS 200B. Color, abaxial surface — Greyed-red, nearest to RHS 183A; main vein is brown, nearest to RHS 200B.

*Leaves borne on the stems.*—Quantity — Approximately 28 leaves per stem. Attachment — Petiolate. Division — Simple. Leaf shape — Deeply palmate, with an average of five deeply cleft lobes, and a reniform to near orbicular profile. Lobes — Depth of sinuses — Deep. Sinus orientation — Convergent. Dimensions — 6.4 cm long, excluding the petiole, and 8.3 cm wide. Leaf attitude — Leaves in an average angle of 90 degrees to the stem. Leaf apex — Acute. Leaf base — Hastate with basal lobes free. Leaf margin — Coarsely serrate. Texture, adaxial and abaxial surfaces — Slightly rugose; pubescent. Pubescence, adaxial surface — Moderately covered with short hairs with an average length of 0.2 mm; colored greyed-white, nearest to RHS 156D. Pubescence, abaxial surface — Sparsely covered with short hairs with an average length of 0.2 mm; colored greyed-white, nearest to RHS 156D. Luster, adaxial surface — Very slightly glossy. Luster, abaxial surface — Very slightly glossy. Color — Juvenile foliage color, adaxial surface — Green, nearest to RHS 143B. Juvenile foliage color, abaxial surface — Yellow-green, nearest to a mixture of RHS 144A and 144B; narrowly margined greyed-orange, nearest to a mixture of RHS 177A and 177B. Mature leaf color, adaxial surface — Greyed-green, nearest to RHS N189A yet slightly darker; narrowly margined and tipped brown, nearest to RHS 200A. Mature leaf color, abaxial surface — Green, nearest to RHS NN137D; narrowly margined and tipped greyed-orange, nearest to a mixture of RHS 178A and 178B. Venation — Type — Palmate. Vein color, adaxial surface — Green, nearest to RHS NN137D. Vein color, abaxial surface — Yellow-green, nearest to RHS N148B. Petiole — Length — 0.5 cm. Diameter — 0.2 cm. Strength — Strong. Texture, adaxial and abaxial surfaces — Sparsely covered with soft hairs, becoming moderately pubescent towards the proximal end of the petiole; average length of hairs is 0.2 cm; colored greyed-white, nearest to RHS 156D. Luster, adaxial and abaxial surfaces — Glossy. Color, adaxial surface — Greyed-purple, nearest to RHS 183B. Color, abaxial surface — Greyed-red, nearest to RHS 178A. Stipules — General — Two leafy stipules present at the base of each leaf. Shape — Ovate. Length — 0.9 cm. Diameter — 0.3 cm. Apex — Acuminate. Base — Broad cuneate. Margins — Serrate. Texture, adaxial and abaxial surfaces — Densely covered with soft hairs; average length of hairs is 0.1 cm; colored white, RHS N155A. Luster, adaxial and abaxial surfaces — Moderately glossy. Color, adaxial surface — Greyed-red, nearest to RHS 183A; main vein is brown, nearest to RHS 200B. Color, abaxial surface — Greyed-red, nearest to RHS 183A; main vein is brown, nearest to RHS 200B.

Inflorescence:

*Habit.*—Dichotomous cyme with two pedicellate flowers borne at the end of the peduncle.

*Natural flowering season.*—Spring into summer in Kirkcudbright, Scotland.

*Time to flower or response time.*—Approximately 9 months.

*Quantity of open flowers per plant.*—12, on average.

*Quantity of flower buds per plant.*—50, on average.

*Quantity of flowers and flower buds per plant.*—62, on average.

*Peduncles.*—Length — Average of 6.0 cm. Diameter — Average of 0.15 cm. Angle — Average angle to stem is 55 degrees. Strength — Moderately strong. Texture — Smooth and densely pubescent; hairs are soft with an average length of 0.8 mm; colored greyed-white, nearest to RHS 156D. Luster — Moderately glossy. Color — Nearest to a mixture of greyed-purple to brown, RHS N186C and 200B.

Flower buds:

*Shape.*—Ovate.

*Length.*—1.3 cm.

*Diameter.*—0.7 cm.

*Texture.*—Densely pubescent; hairs are soft with an average length of 0.5 mm; colored white, nearest to RHS N155A.

*Luster.*—Matte.

*Color.*—Green, nearest to RHS 138B; axially striped with brown, nearest to RHS N200A; apex is suffused with purple, nearest to RHS N78A.

Flower:

*Shape, type.*—Rotate; single.

*Flowering habit.*—Freely flowering.

*Aspect.*—Upright to outward.

*Flower longevity on plant.*—Approximately seven days.

*Persistent or self-cleaning.*—Self-cleaning.

*Fragrance.*—Non-fragrant.

*Diameter.*—5.3 cm.

*Depth.*—1.2 cm.

*Pedicels.*—Length — 2.6 cm. Diameter — 0.1 cm. Angle — Average angle to peduncle is approximately 55 degrees. Strength — Moderately strong. Texture — Smooth and densely pubescent; hairs are soft with an average length of 0.8 mm; colored greyed-white, nearest to RHS 156D. Luster — Moderately glossy. Color — Greyed-brown, nearest to RHS 199B; underside is darker, nearest to RHS N199B.

*Calyx.*—Shape — Rotate. Length — 0.7 cm. Diameter — 2.1 cm. Sepals — Arrangement — Rotate; one whorl of sepals which alternate between broad sepals and narrow sepals. Quantity — 5 unfused sepals; 5 broad sepals and 5 narrow sepals. Shape — Ovate. Aspect — Slightly concave. Dimensions — 1.4 cm long and 0.6 cm wide. Apex —

Mucronate. Base — Cuneate. Margin — Entire; no undulation. Texture and luster, upper surface — Smooth, pubescent, and moderately glossy; densely covered with short, glandular hairs with an average length of 0.5 mm and colored greyed-white, nearest to RHS 156D. Texture and luster, lower surface — Smooth, pubescent, and matte; densely covered with short, glandular hairs with an average length of 0.5 mm and colored greyed-white, nearest to RHS 156D. Color — When opening, upper surface — Yellow-green, nearest to RHS 144A; margins are lighter and translucent, nearest to RHS 145D; tipped brown, nearest to RHS 200B. When opening, lower surface — Yellow-green, nearest to RHS 146B; margined greyed-purple, nearest to RHS 183B; tipped brown, nearest to RHS 200B. Fully opened, upper surface — Yellow-green, nearest to RHS 144A; margins are lighter and translucent, nearest to RHS 145D; tipped brown, nearest to RHS 200B; not fading. Fully opened, lower surface — Yellow-green, nearest to RHS 146B; margined greyed-purple, nearest to RHS 183B; tipped brown, nearest to RHS 200B; not fading. Venation — Fully opened, upper surface — Yellow-green, nearest to RHS 144A. Fully opened, lower surface — Greyed-purple, nearest to RHS 183B.

*Petals*.—Quantity — Five. Arrangement — Rotate; arranged in a single whorl of unfused petals. Length — 2.8 cm. Width — 2.5 cm. Shape — Broad obovate. Apex — Rounded. Base — Narrow cuneate. Margin — Entire; lightly undulated. Texture, upper surface — Glabrous, moderately velvety and matte; base is glossy. Texture, lower surface — Glabrous, slightly velvety, and matte. Petal color — When opening, upper surface — Purple, nearest to a mixture of RHS N78A and NN78A; veined black, nearest to RHS 203D. When opening, lower surface — Purple, nearest to a mixture of RHS N78B and NN78C; veined violet-blue to black, nearest to a mixture of RHS N92A and 203B. Fully opened, upper surface — Purple, nearest to a mixture of RHS N78A and NN78A; veined black, nearest to RHS 203D. Fully opened, lower surface — Purple, nearest to RHS NN78A; veined violet-blue to black, nearest to a mixture of RHS N92A and 203B. When faded, upper surface — Purple-violet, nearest to RHS N81A; veined black, nearest to RHS 203D. When faded, upper surface — Purple-violet, nearest to a mixture of RHS N81B N82A; veined black, nearest to RHS 203D.

Reproductive organs:

*Androecium*.—Stamens — Quantity — Approximately 10. Anthers — Shape — Oblong. Dimensions — 0.2 cm long and 0.1 cm wide. Color — Nearest to a mixture of brown and black, RHS 200A and 203A. Filaments — Length — 0.8 cm. Color — Greyed-purple, nearest to RHS N186C; fading to yellow-green towards the base, nearest to RHS 145C. Amount of Pollen — Sparse. Pollen color — Yellow, nearest to RHS 11B.

*Gynoecium*.—Pistil — Quantity — One. Length — 0.5 cm. Style — Length — 0.45 cm. Color — Nearest to a mixture of violet-blue and greyed-purple, RHS N92A and N186C. Stigma — Quantity — Five. Shape — Curled. Length — 0.15 cm. Diameter — 0.6 cm. Color — Nearest to a mixture of violet-blue and greyed-purple, RHS N92A and N186C. Ovary Color — Greyed-purple, nearest to RHS 183B.

Seed and fruit:

*Fruit*.—Shape — Oblong. Quantity — 62. Dimensions — 2.8 cm long and 0.6 cm in diameter. Texture — Densely covered with short glandular hairs with an average length of 0.8 mm and colored greyed-white, nearest to RHS 156D. The glandular tip is generally colored with a mixture of greyed-red and greyed-purple; the structure is too minute as to accurately record color designations. Color, mature fruit — Greyed-orange, nearest to RHS 173A, and axially striped with yellow-green, nearest to RHS 151C. Persistent styles and stigmas are colored with a mixture of violet-blue and greyed-purple, nearest to RHS N92A and N186C yet slightly darker.

*Seed*.—No seeds have been detected.

COMPARISONS WITH THE PARENT PLANTS

Plants of the new cultivar 'MACGER001' differ from its seed parent, an unnamed *Geranium pratense* (not patented), by the characteristics described in Table 1.

TABLE 1

| Characteristic | 'MACGER001' | The seed parent. |
|---|---|---|
| General coloration of the foliage. | Lighter green by comparison to the seed parent, and suffused with a bronze coloration. | Darker green by comparison to 'MACGER001'. |
| General coloration of the flower. | Darker red-purple by comparison to the seed parent. | Lighter red-purple by comparison to 'MACGER001'. |
| General coloration of the flower eye. | Darker purple by comparison to the seed parent. | Lighter purple by comparison to 'MACGER001'. |

Plants of the new cultivar 'MACGER001' may be distinguished from its pollen parent, an unnamed *Geranium psilostemon* plant (not patented), by the characteristics described in Table 2.

TABLE 2

| Characteristic | 'MACGER001' | The pollen parent |
|---|---|---|
| General coloration of the foliage. | Darker green by comparison to the pollen parent, and suffused with a bronze coloration. | Lighter green by comparison to 'MACGER001'. |
| General coloration of the flower. | Lighter red-purple by comparison to the pollen parent. | Darker red-purple by comparison to 'MACGER001'. |
| General coloration of the flower eye. | Darker purple by comparison to the pollen parent. | Lighter purple by comparison to 'MACGER001'. |

COMPARISON WITH THE MOST SIMILAR VARIETY OF COMMON KNOWLEDGE

Plants of the new cultivar 'MACGER001' may be distinguished from the most similar known commercial comparator, *Geranium pratense* x *G. psilosetum* 'Eva' (not patented), by the characteristics described in Table 3.

TABLE 3

| Characteristic | 'MACGER001' | 'Eva' |
|---|---|---|
| General coloration of the mature foliage. | Greyed-green, suffused with a bronze coloration. | Green. |
| General coloration of the foliar margins. | Greyed-purple. | Green. |

TABLE 3-continued

| Characteristic | 'MACGER001' | 'Eva' |
|---|---|---|
| General coloration of the flower. | Darker red-purple by comparison to 'Eva'. | Lighter red-purple by comparison to 'MACGER001'. |

That which is claimed is:

1. A new and distinct cultivar of *Geranium* plant named 'MACGER001', substantially as described and illustrated herein.

* * * * *